US00PP11755P2

(12) United States Plant Patent
VandenBerg

(10) Patent No.: US PP11,755 P2
(45) Date of Patent: Jan. 30, 2001

(54) CHRYSANTHEMUM PLANT NAMED 'YOSPRINGFIELD'

(75) Inventor: Cornelis P. VandenBerg, Salinas, CA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/275,118

(22) Filed: Mar. 24, 1999

(51) Int. Cl.[7] ..... A01H 5/00
(52) U.S. Cl. ..... Plt./287
(58) Field of Search ..... Plt./287, 291

*Primary Examiner*—Howard J. Locker
(74) *Attorney, Agent, or Firm*—C. A. Whealy

(57) ABSTRACT

A distinct cultivar of Chrysanthemum plant named 'Yospringfield', characterized by its upright, somewhat spreading, compact and uniformly mounded plant habit; freely branching habit; dark green leaves; uniform and very early flowering; large decorative disbud-type inflorescences that are about 11.5 cm in diameter; attractive lavender pink ray florets; and excellent postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yospringfield.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in August, 1994, in Salinas, Calif., of the *Dendranthema grandiflora* cultivar Charm, disclosed in U.S. Plant Pat. No. 5,502, as the female, or seed, parent, with a proprietary Chrysanthemum seedling selection identified as code number YB-6145, as the male, or pollen, parent.

The new Chrysanthemum was discovered and selected by the Inventor as a flowering plant within the progeny of the stated cross in a controlled environment in Fort Myers, Fla., in November, 1995. The selection of this plant was based on its desirable inflorescence form and floret colors and good post-production longevity.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Yospringfield has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yospringfield'. These characteristics in combination distinguish 'Yospringfield' as a new and distinct Chrysanthemum:

1. Upright, somewhat spreading, compact and uniformly mounded plant habit.
2. Freely branching habit.
3. Dark green leaves.
4. Uniform and very early flowering.
5. Large decorative disbud-type inflorescences that are about 11.5 cm in diameter.
6. Attractive lavender pink ray florets.
7. Excellent postproduction longevity with inflorescences and leaves maintaining good substance and color for about three or four weeks in an interior environment.

The new Chrysanthemum can be compared to the parent Chrysanthemum cultivar Charm. However in side-by-side comparisons in Salinas, Calif., and Leamington, Ontario, Canada, under commercial practice, plants of the new Chrysanthemum differed from plants of the cultivar Charm in the following characteristics:

1. Plants of the new Chrysanthemum are less vigorous and shorter than plants of the cultivar Charm. Plants of the new Chrysanthemum require an additional week of long days to achieve the same finished height as plants of the cultivar Charm.
2. Plants of the new Chrysanthemum have slightly larger inflorescences than plants of the cultivar Charm.
3. Plants of the new Chrysanthemum flower about one week earlier than plants of the cultivar Charm.
4. Ray florets of plants of the new Chrysanthemum are narrower, longer and more numerous than ray florets of plants of the cultivar Charm.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yospringfield'.

The photograph at the bottom of the first sheet comprises a close-up view of upper (left) and lower (right) surfaces of typical inflorescences and upper (left) and lower (right) surfaces of typical leaves of the cultivar Yospringfield.

The photograph at the top of the second sheet comprises a side perspective view of typical flowering plants of 'Yospringfield' (left) and 'Charm' (right).

The photograph at the bottom of the third sheet comprises a close-up view of upper surfaces of typical inflorescences and leaves of plants of 'Yospringfield' (left) and 'Charm' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yospringfield.

Commercial classification: Decorative disbud-type pot Chrysanthemum.

Parentage:

*Female or seed parent.*—*Dendranthema grandiflora* cultivar Charm, disclosed in U.S. Plant Pat. No. 5,502.

*Male or pollen parent.*—Proprietary *Dendranthema grandiflora* seedling selection identified as code number YB-6145.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative disbud-type pot Chrysanthemum. Inverted triangle; stems mostly upright and somewhat outwardly spreading; uniformly mounded appearance to the plant. Freely branching; about four lateral branches develop after removal of terminal apex (pinching).

*Plant height.*—About 27 cm.

*Plant width.*—About 40 cm.

*Stem color.*—147A/147B.

*Stem texture.*—Pubescent.

*Foliage description.*—Arrangement: Alternate. Length: About 9.6 cm. Width: About 6.6 cm. Apex: Mucronate. Base: Attenuate. Margin: Palmately lobed, sinuses between lateral lobes mostly parallel. Texture: Upper and lower surfaces with very fine pubescence; veins prominent on lower surface. Petiole length: About 2.1 cm. Color: Young foliage upper surface: Darker than 147A. Young foliage lower surface: Slightly darker than 147B. Mature foliage upper surface: Darker than 147A. Mature foliage lower surface: Slightly darker than 147A. Venation upper surface: 147B. Venation lower surface: Close to 147B.

Inflorescence description:

*Appearance.*—Decorative disbud-type inflorescence form with elongated oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about seven weeks later.

*Postproduction longevity.*—Inflorescences and leaves will maintain good color and substance for about three or four weeks in an interior environment.

*Quantity of inflorescences.*—As a disbud-type, all lateral inflorescences are removed to allow for maximum terminal inflorescence size. One inflorescence per lateral stem; about four inflorescences per plant.

*Inflorescence bud.*—Height: About 6 mm. Diameter: About 8 mm. Color: Close to 147A.

*Inflorescence size.*—Diameter: About 11.5 cm. Depth (height): About 2.8 cm. Diameter of disc: About 7 mm, inconspicuous.

*Ray florets.*—Shape: Elongated oblong with short corolla tube. Orientation: Initially upright then perpendicular to peduncle. Aspect: Straight; mostly concave. Length: About 5.7 cm. Width: About 1.2 cm. Apex: Rounded to emarginate. Margin: Entire. Texture: Smooth, glabrous, satiny. Number of ray florets per inflorescence: About 293. Color: When opening: Initially white, then lavender pink, 75A–75B. Fully opened, upper surface: Lavender pink, 75A–75B. Fully opened, lower surface: Light lavender pink, 75C–75D.

*Disc florets.*—Shape: Tubular. Apex: Serrated. Length: About 6 mm. Width: Apex: About 1.3 mm. Base: About 1 mm. Number of disc florets per inflorescence: About 45. Color: Immature: Greener than 154A. Mature: Apex: 9A. Base: White, 155D.

*Reproductive organs.*—Androecium: Present on disc florets only. Anther color: 13A. Pollen: Amount: Scarce. Color: Close to 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yospringfield', as illustrated and described.

* * * * *

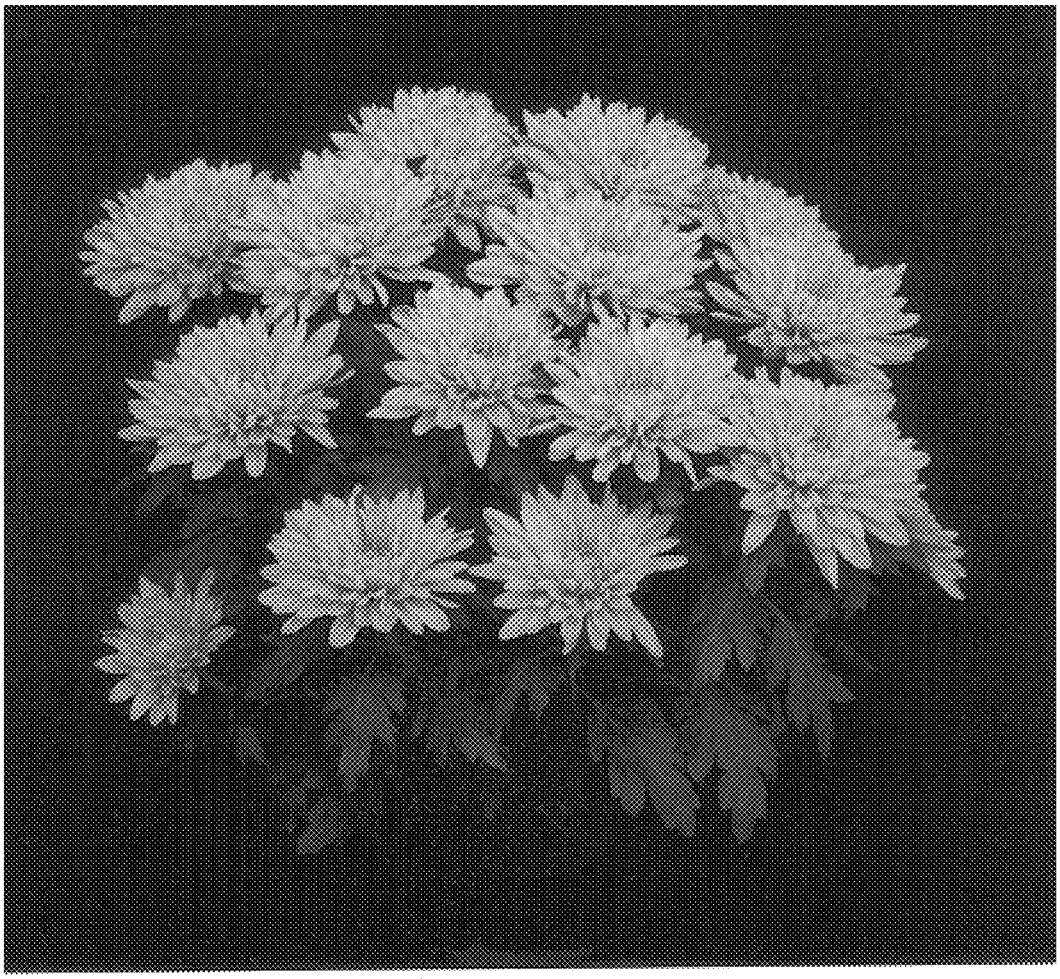
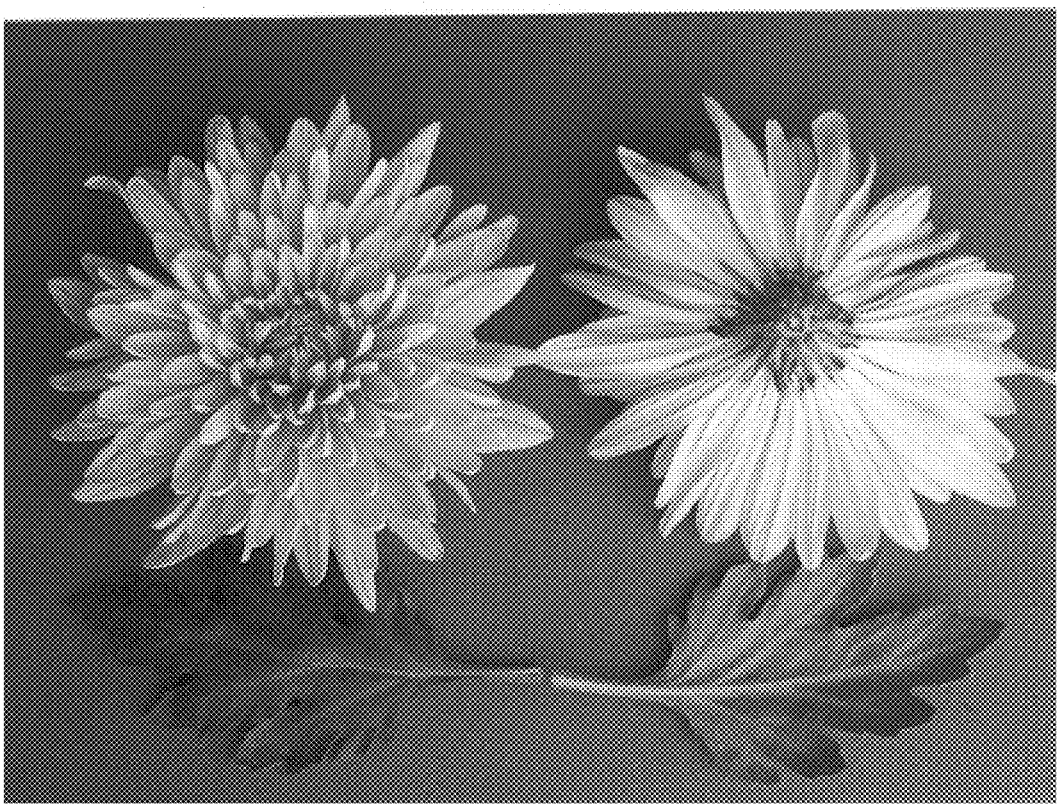

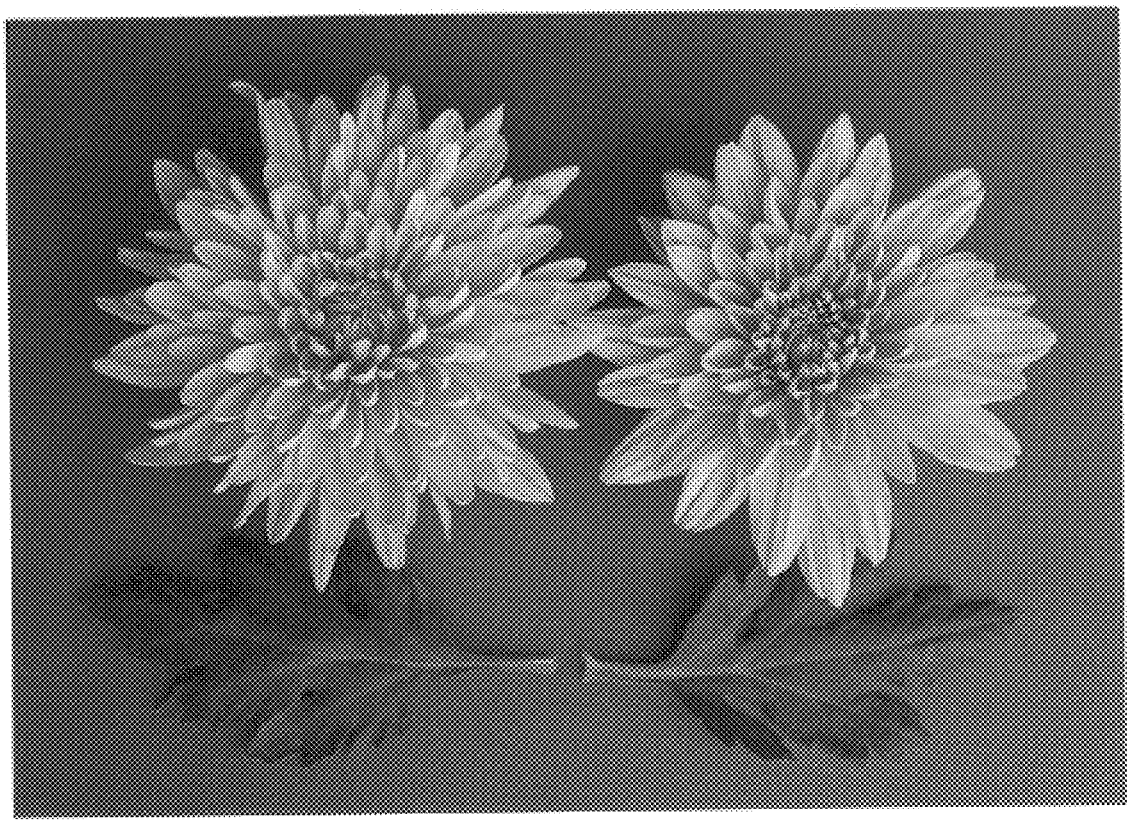

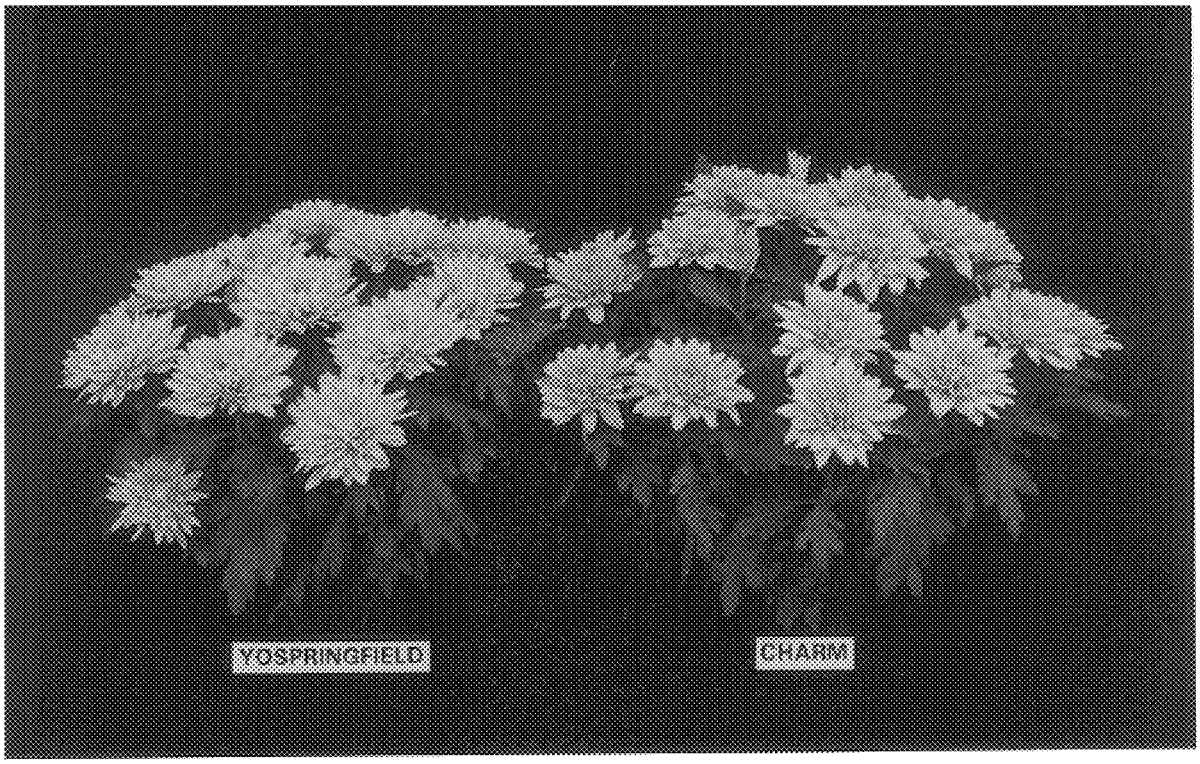
YOSPRINGFIELD
CHARM